United States Patent
Seddigi et al.

(10) Patent No.: US 9,283,546 B2
(45) Date of Patent: Mar. 15, 2016

(54) COMPOSITION OF PHOTOCATALYST AND METHOD OF USING THE SAME FOR DEGRADATION OF FUEL WASTE IN CONTAMINATED WATER

(71) Applicant: Umm Al-Qura University, Makkah (SA)

(72) Inventors: Zaki S Seddigi, Makkah (SA); Saleh A Saleh, Makkah (EG)

(73) Assignee: Umm-Al-Qura University, Makkah (SA)

( * ) Notice: Subject to any disclaimer, the term of this patent is extended or adjusted under 35 U.S.C. 154(b) by 0 days.

(21) Appl. No.: 13/949,662

(22) Filed: Jul. 24, 2013

(65) Prior Publication Data

US 2015/0031140 A1 Jan. 29, 2015

(51) Int. Cl.
*G01N 31/22* (2006.01)
*G01N 31/00* (2006.01)
*B01J 23/44* (2006.01)
*B01J 23/60* (2006.01)
*B01J 35/00* (2006.01)

(52) U.S. Cl.
CPC *B01J 23/60* (2013.01); *B01J 23/44* (2013.01); *B01J 35/002* (2013.01); *B01J 35/004* (2013.01); *G01N 31/00* (2013.01); *G01N 31/22* (2013.01); *Y10T 436/20* (2015.01); *Y10T 436/200833* (2015.01)

(58) Field of Classification Search
CPC ....... G01N 31/22; G01N 31/00; G01N 33/64; G01N 33/52; G01N 33/493; Y10T 436/00; Y10T 436/20; Y10T 436/200833
USPC ........... 436/128, 127; 252/176, 175; 423/622, 423/592.1, 579
See application file for complete search history.

(56) References Cited

U.S. PATENT DOCUMENTS 5,817,896 A * 10/1998 Thomson ............ 570/176

OTHER PUBLICATIONS

Sahoo, Suchismita et al, Effect of Zinc Oxide Nanoparticles as Cure Activator on the Properties of Natural Rubber and Nitrile Rubber, Journal of Applied Polymer Science, 2007, vol. 105, pp. 2407-2415.*
Wang Jinmin, et al, Synthesis and characterization of ZnO nanoparticles assembled in one-dimensional order, Inorganic Chemistry Communnications, 2003, 6, , pp. 877-881.*
Siddiqui, Mohammad N. et al, Laser-based photo-oxidative degradation of methyl tertiary-butyl ether (MTBE) using zinc oxide (ZnO) catalyst, Journal of Environmental Science and Health Part A, 2011, 46, pp. 1154-1159.*
Seddigi, Zaki S. et al, Preparation and characterization of Pd doped ceria-ZnO nanocomposite catalyst for methyl tert-butyl ether (MTBE) photodegredation, Journal of Hazardous Materials, 2014, 264, pp. 71-78.*
Hosseini-Sarvari Mona et al, Palladium supported on zinc oxide nanoparticles: Synthesis,characterization, and application as heterogeneous catalyst for Mizoroki—Heck and Sonogashira reactions under ligand-free and air atmosphere conditions, Applied Catalysis A: General, 2014, 475, pp. 477-486.*
Ibrahim, Mohamed M., et al, Carbon nanotube/titanium nanotube composites loaded platinum nanoparticles as high performance photocatalysts, Applied Catalysis A: General, 2014, 475, pp. 90-97.*

* cited by examiner

*Primary Examiner* — Christine T Mui
(74) *Attorney, Agent, or Firm* — Geeta Kadambi; Riddhi IP LLC

(57) ABSTRACT

The present disclosure relates to a novel photocatalyst composition and a process of using the photocatalyst for the photocatalytic degradation of methyl tertiary-butyl ether (MTBE) in water. Palladium doped nano zinc oxide photocatalyst was prepared by zinc nitrate hexahydrate and an ammonium carbonate and the photocatalyst composition demonstrated more than 90-99% degradation of MTBE at room temperatures in a photo catalytic reaction conducted in an oxygen saturated aqueous medium.

8 Claims, 4 Drawing Sheets

COMPOSITION OF PHOTOCATALYST AND METHOD OF USING THE SAME FOR DEGRADATION OF FUEL WASTE IN CONTAMINATED WATER

FIELD OF TECHNOLOGY

The present invention relates generally to a novel composition of a photocatalyst and method of using the photocatalyst for photodegradation of ether-based compounds in water. More specifically, the present invention relates to a novel composition of palladium doped nano zinc oxide (Pd/nano ZnO) photocatalyst and use of the photocatalyst for photodegradation of methyl tertiary-butyl ether (MTBE) in water.

BACKGROUND

Methyl tertiary-butyl ether (MTBE) has been introduced as an additive for unleaded gasoline since the 1980's by the US Environmental Protection Agency (US EPA). It was licensed as a lead replacement because of the potential accumulation of lead in the environment and adversely affects human health. MTBE has been known to increase octane and oxygen levels in gasoline and thus reduces pollution from petroleum products emission.

Owing to its widespread use, MTBE has now been found to be in contamination levels in underground water, surface and also in the air near some fuel facilities. There are a number of sources through which MTBE is released into underground water: leakage from petrol storage and distribution tanks, spills, drips, lawnmowers, emission from marine engines into lakes, from air deposition, leaks from pipelines and above ground storage tanks. MTBE is highly inflammable, soluble in water, not easily absorbed in soil, moves along with ground water and resists biodegradation which makes it a difficult contaminant to work with. Being highly hydrophilic in nature, removal of MTBE from water from commonly used and known methods is ineffective and costly.

Some of the known methods are absorption on activated carbon, use of air stripping, biological degradation (Vandenbergh et. al., 2006; Salanitro Joseph et. al., 2002) ultra violet/hydrogen peroxide ($UV/H_2O_2$) process (Stefan et al. 2000) among others. However, none of the treatments have provided a complete and safe solution for the removal of MTBE from contaminated sources.

SUMMARY

In the present disclosure a novel composition of a photocatalyst and a process of using the photocatalyst for the photocatalytic degradation of fuel contamination in water are disclosed. Further, the present invention relates to a novel composition of a photocatalyst and a process of using the photocatalyst for the photocatalytic degradation of MTBE in water.

In one embodiment, the photocatalyst as disclosed in present application is a metal doped nano zinc oxide (nano ZnO) photocatalyst. In another embodiment, the photocatalyst as disclosed in present application is platinum group metal doped nano ZnO photocatalyst. In another embodiment, it is a palladium doped nano ZnO photocatalyst.

In one embodiment, a method of synthesizing nano ZnO particles from zinc nitrate hexahydrate and ammonium carbonate in aqueous solution is described. In another embodiment, a zinc nitrate hexahydrate and an ammonium carbonate are mixed in pre-determined ratios in aqueous solution. In preferred embodiment, the zinc nitrate hexahydrate and ammonium carbonate are mixed in equal molar ratios in aqueous solution.

In several embodiments, a process of calcination is performed at a temperature range of 400° C. to 600° C. and between 4 hrs to 8 hrs at a heating rate of 1-2° C./min to obtain nano ZnO. In preferred embodiment, the process of calcination is performed at 500° C. for 6 hrs at a heating rate of 1° C./min to obtain nano ZnO.

In one embodiment, a metal is doped onto synthesized nano ZnO particles to obtain metal nano ZnO photocatalyst. In most embodiments, the metal used is palladium to obtain palladium/nano ZnO photocatalyst.

In one embodiment, a pre-determined amount of palladium is dissolved in de-ionized water to form solution required to cover nano ZnO powder to form a palladium nitrate impregnated nano ZnO. The palladium nitrate impregnated nano ZnO is then dried overnight. In one embodiment, palladium nitrate impregnated nano ZnO is further exposed to ammonia vapors. Further, palladium nitrate impregnated nano ZnO undergo calcination to synthesize Pd/nano ZnO photocatalyst.

In one embodiments, a process of calcination is performed at a temperature range of 400° C. to 600° C. and between 3 hrs to 6 hrs at a heating rate of 1-2° C./min to obtain Pd/nano ZnO photocatalyst. In preferred embodiment, the process of calcination is performed at 500° C. for 3 hrs at a heating rate of 1.5° C./min to obtain Pd/nano ZnO photocatalyst.

In one embodiment, palladium in the weight ranging from 0.5% to 1.5% is used for doping onto nano ZnO particles. In another embodiment, 0.5% by weight palladium is doped onto nano ZnO particles. In another embodiment, palladium 1.0% by weight is doped onto nano ZnO particles. In another, embodiment, palladium 1.5% by weight is doped onto nano ZnO particles.

In one embodiment, the photocatalyst as disclosed in present application is prepared by wetness incipient impregnation method. The wetness incipient impregnation method is achieved by wetting a support with a solution of a metal salt. An attractive feature of wetness impregnation and drying is that no wastewater is produced and that loss of active component with wastewater is not possible. Especially with precious metals, the negligible risk of losing active component is highly advantageous.

In a typical procedure of making Pd/nano ZnO photocatalyst, a predetermined amount of palladium (II) nitrate dihydrate ($Pd(NO_3)_2.2H_2O$) was dissolved in deionized water to form enough solution to cover the required amount of nano-ZnO powder. The palladium nitrate impregnated nano-ZnO was dried at heating rate of 1° C./min from room temperature up to 100° C. and then exposed to ammonia vapors for 10 minutes. This step is performed to avoid melting of palladium nitrate before decomposition resulting high dispersion of nano-Pd particles on ZnO. The mixture was dried overnight in air at 110° C. The dried Pd/ZnO precursor was calcined at 500° C. for 3 hours at a heating rate of 1.5° C./min to obtain Pd-nano ZnO photocatalyst.)

In one embodiment, a method of using Pd/nano ZnO photocatalyst for photocatalytic degradation of impurities in water is described. In another embodiment, the method of using Pd/nano ZnO photocatalyst for photocatalytic degradation of MTBE in water is described.

In one embodiment, a pre-determined amount of metal doped nano ZnO photocatalyst is added into deionized water. In another embodiment, a pre-determined amount of Pd/nano ZnO photocatalyst is added into deionized water containing MTBE. The sample containing MTBE and Pd-nano ZnO photocatalyst is loaded into a photochemical reactor.

In one embodiment, the solution to be analyzed in loaded onto two side arms photochemical reactor. In another embodiment the solution to be analyzed in loaded onto two side arms quartz photochemical reactor.

In one embodiment, the photochemical reactor has a cooling water system running throughout the photodegradation process. In another embodiment, the photochemical reactor has a cooling water system running for prescribed duration during photodegradation process.

In one embodiment, an inert gas is bubbled into the solution at an appropriate rate and time to saturate the solution. In preferred embodiment, oxygen is bubbled into the solution at an appropriate rate and time to saturate the solution.

In one embodiment, the photochemical reactor is equipped with gas inlet tube preferably oxygen. Oxygen is bubbled into the photochemical reactor at a rate of about 50 cc/minute for a period of 30 minutes with continuous stirring.

In one embodiment, saturated sample is exposed to UV light source for a specific time period. In another embodiment, saturated sample containing MTBE is exposed to UV light source for a specific time period.

In one embodiment, the UV lamp is fitted with long-teflon tube inserted into the solution in photochemical reactor. In another embodiment, the UV lamp is high pressure mercury lamp. The UV lamp is powered ON for a specific period of time in the photochemical reactor. In one embodiment, the photocatalyst is added before UV lamp is powered ON whereas in another embodiment, the photocatalyst is added after the UV lamp is powered ON and the solution is exposed for a required period of time.

In one embodiment, oxygen inlet tube is removed before UV lamp is powered ON whereas in another embodiment, oxygen inlet tube is removed after UV lamp is powered ON.

In one embodiment, samples are collected at regular intervals and samples are characterized by gas chromatography equipped with flame ionization detector. In another embodiment, samples are characterized using known methods in the art.

In one embodiment, a process of photocatalytic degradation of MTBE in water is described. The process is carried out by a mixing a pre-determined amount of Pd/nano ZnO photocatalyst into deionized water containing MTBE to form a solution. The solution is then loaded into the photochemical reactor. The solution is thoroughly stirred to evenly distribute the photocatalyst into the solution. A liquid sample is then collected and designated as initial concentration of MTBE. The solution is further saturated by passing oxygen gas from the solution. The solution is exposed to UV light for a particular time period and liquid samples are collected periodically. MTBE concentration is calculated in the liquid samples using gas chromatography with flame ionization detector.

The novel composition of photocatalyst and method of using the photocatalyst for degradation of MTBE in water, disclosed herein, may be implemented in any means for achieving various aspects. Other features will be apparent from the accompanying figures and from the detailed description that follows.

BRIEF DESCRIPTION OF THE DRAWINGS

Example embodiments are illustrated by way of example and no limitation in the graph and in the accompanying figures, like references indicate similar elements and in which.

Other features of the present embodiments will be apparent from the accompanying detailed description that follows.

DETAILED DESCRIPTION

The present disclosure relates to a novel composition of a photocatalyst, method of making the photocatalyst and using the photocatalyst for the photocatalytic degradation of MTBE in water.

Synthesis of nano zinc oxide (nano ZnO)

There are a number of commercial and non-commercial procedures available for the preparation of nano ZnO particles and a person skilled in the art can use any one of the processes for the preparation of nano ZnO particles.

Nano ZnO particles can be prepared using sol-gel method (Fernandesa et al. 2009), through following steps: The zinc nitrate hexahydrate and polyvinyl alcohol (PVA) aqueous solutions of required molar ratio were prepared by dissolving stiochiometric amounts zinc nitrate hexahydrate and PVA in deionized water. The two prepared solutions were mixed under continuous stirring at room temperature for 2 hours. Subsequently, the mixed solution was heated at a temperature of 80° C. for 24 hours to obtain a gel. The gel was dried at 100° C. for 24 hours and ground into a fine powder. The powdered dried gel was calcined at a rate 1° C./minute for 6 hours to obtain nano ZnO particles.

Figure 1:
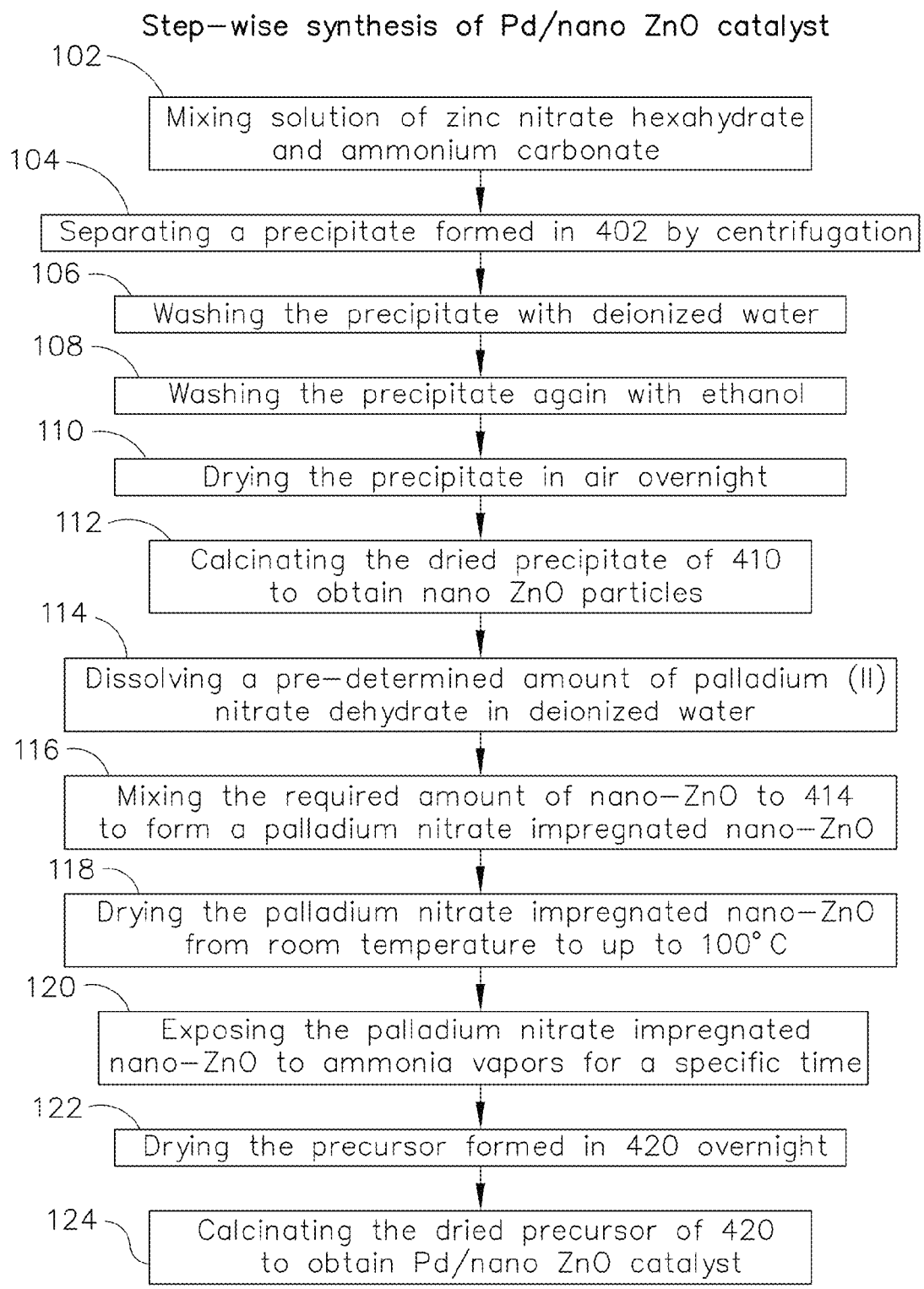
FIG. 1 shows a flow chart for method of making Pd/nano ZnO photocatalyst.

In the instant invention, synthesis of nano ZnO particles is by using aqueous solution of required molar ratios of zinc nitrate hexahydrate and ammonium carbonate 402 and mixing with continuous stirring at room temperature for 2 hours. A precipitate is then formed and separated by centrifugation 404. The prepared precipitate is thoroughly washed with de-ionized water 406 and then with ethanol 408. The prepared precipitate is then dried in air at 100° C. overnight 410. The dried ZnO precursor is further calcined at 500° C. for 6 hours to obtain nano-ZnO particle 412 (FIG. 1).

Alternatively, nano sized ZnO can also be procured from known commercial sources.

Synthesis of Pd/nano ZnO Photocatalyst

The nano ZnO (as described above) is further treated for the preparation of a photocatalyst of the present invention. The method include mixing a pre-determined amount of palladium(II) nitrate dihydrate ($Pd(NO_3)_2.2H_2O$) in deionized water 414 to form enough solution to cover the required amount of nano-ZnO powder and form palladium nitrate impregnated nano-ZnO 416. The palladium nitrate impregnated nano-ZnO was then dried at heating rate of 1° C./min from room temperature up to 100° C. 418 and then exposed to ammonia vapors for another 10 min 420. This step is performed to avoid melting of palladium nitrate before decomposition resulting in high dispersion of nano Pd particles on ZnO. The palladium nitrate impregnated nano-ZnO was then dried overnight in air at a temp of 110° C. 422. The dried palladium nitrate impregnated nano-ZnO was calcined at 500° C. for 3 hours at a heating rate of 1.5° C./min to obtain a Pd-nano ZnO photocatalyst 424 (FIG. 1).

Palladium is doped on the synthesized nano ZnO using wetness incipient impregnation method. Palladium in the w % range of 0.5%-1.5% is used for the degradation of MTBE in water.

Photodegradation of MTBE in Water

Figure 2:
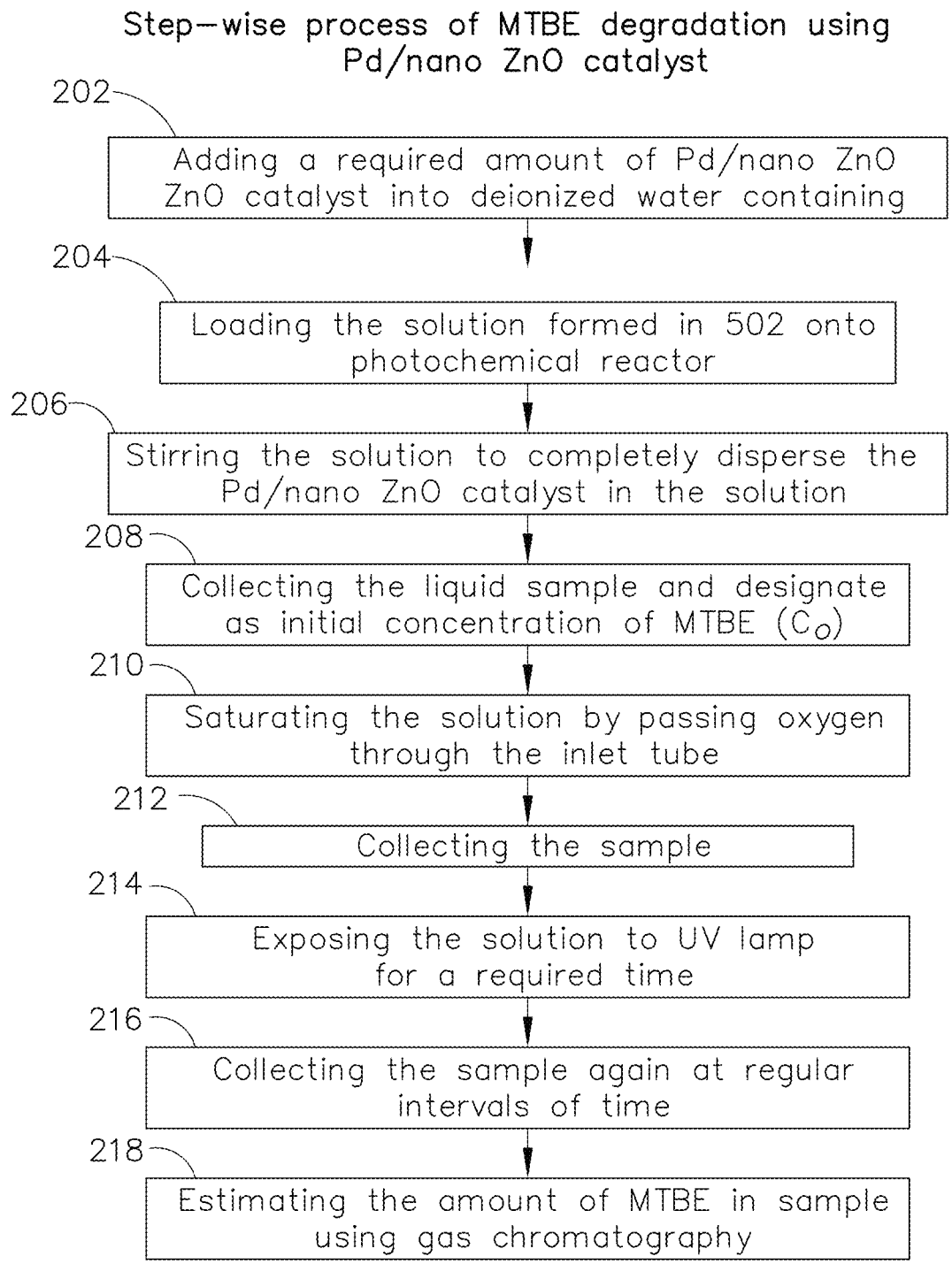
FIG. 2 shows in a flow chart for method of using Pd/nano ZnO photocatalyst for photodegradation of MTBE in water.

Photodegradation of MTBE was carried out by using the Pd-nano ZnO photocatalyst as synthesized above. To carry out photodegradation, a required amount of Pd/nano ZnO photocatalyst was added into deionized water containing MTBE contamination 502. The solution thus formed was loaded onto the photochemical reactor 504. The solution was stirred thoroughly to disperse the Pd/nano ZnO photocatalyst in the solution 506. Following this, a liquid sample was collected and designated as initial concentration of MTBE ($C_o$) 508. After collecting the sample, remaining solution was saturated by passing oxygen through the inlet tube into the solution 510. Again the sample was collected 512. The oxygen inlet tube was taken out of the photochemical reactor and UV lamp was powered ON for a particular time period 514. The samples were again collected at regular intervals of time 516 and the amount of MTBE was calculated using gas chromatography equipped with flame ionization detector 518 (FIG. 2).

The photochemical reactor being used for the photodegradation process is a double sided arms quartz photochemical reactor. The reactor is further fitted with a cooling jacket which runs the cooling water throughout the experiment or for a prescribed time depending on the experimental conditions. The temperature of the cooling water system is set at 25° C. using a thermostatic water circulating bath. The temperature of the cooling water system may be set above or below 25° C. depending on the experimental conditions.

The photochemical reactor further comprises of a UV lamp, preferably a mercury lamp. A 125 wt. UV high pressure mercury lamp is fitted along with long Teflon tube. The assembly of lamp and Teflon tube is inserted into the reaction solution. The photochemical reactor further comprises of an oxygen inlet tube. The tube provides the necessary oxygen to saturate the reaction solution.

To carry out photodegradation, the following procedure can also be followed: In a 500 ml two side arms photochemical reactor fitted with a cooling jacket, 500 ml of distilled water, 100 mg of the selected photocatalyst and 100 ppm by weight of MTBE were stirred at room temperature without UV light for 30 min to have complete dispersion of the photocatalyst in the solution and a liquid sample was collected to be designated as initial concentration of MTBE ($C_o$). Then, a current of Oxygen gas with a rate of 50 cc/min was passed through the solution via inlet tube for 30 min and sample was collected. The oxygen inlet tube was then removed and the UV lamp was switched ON and the system was covered with aluminum foil. Samples were then collected every hour to calculate the concentration of MTBE.

EXAMPLES

The present embodiments are being described with reference to specific example embodiments and are included to illustrate but not limit the scope of the invention.

Example 1

Degradation of MTBE in water without adding a photocatalyst: In the present experiment, no photocatalyst was used and the effect of only UV light on the degradation of MTBE in water was investigated. A solution of 100 ppm by weight of MTBE was placed in a photochemical reactor. The solution was saturated with bubbling oxygen at a rate of about 50 cc/minute for a period of 30 min with continuous stirring. UV lamp was powered ON and a first liquid sample was taken after 1 hour of exposure to UV light. The experiment was run for a period of 5 hours and the liquid samples were withdrawn after every hour. The samples were then analyzed for the concentration of MTBE using gas chromatograph equipped with flame ionization detector (FID).

Figure 3:
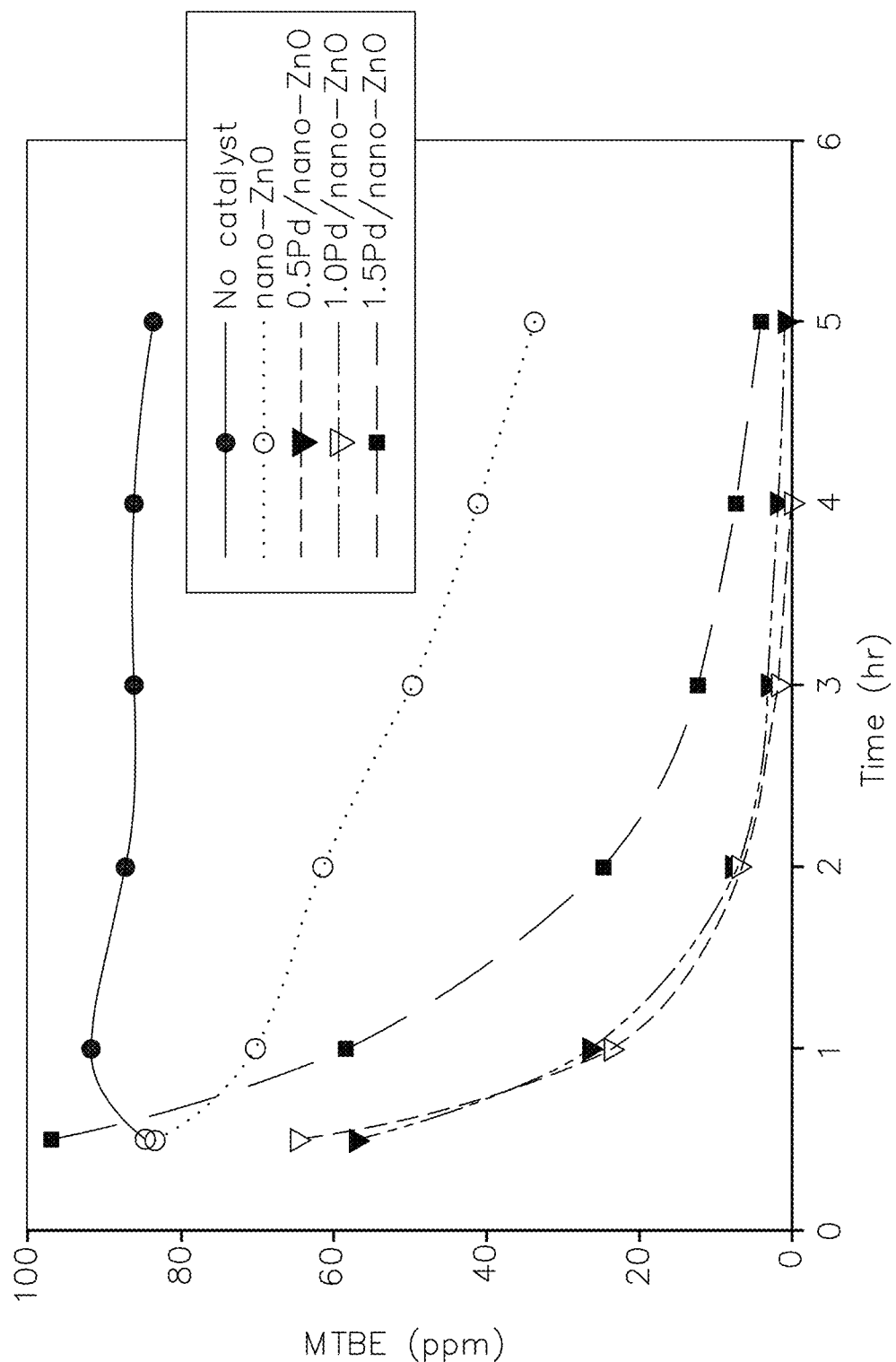
FIG. 3 shows results of MTBE photocatalytic degradation under various experimental conditions.

The results are shown in FIG. 3. The results show almost negligible degradation of MTBE after 5 hours of UV exposure.

Example 2

Preparation of nano-ZnO particles and using the same as a photocatalyst to study degradation of MTBE in water: Nano-ZnO particle was prepared by mixing the aqueous solution of required molar ratios of zinc nitrate hexahydrate and ammonium carbonate (molar ratio of 1:1) with continuous stifling at room temperature for a period of 2 hours. A precipitate was formed and separated by centrifugation. The prepared precipitates were thoroughly washed with de-ionized water followed by ethanol. The prepared precipitates then were dried in air at 100° C. overnight. The dried ZnO precipitates were calcined at 500° C. for 6 hours at a heating rate of 1° C./min, to obtain nano-ZnO particles.

Nano-ZnO particles were then used as a photocatalyst to investigate the photocatalytic degradation of MTBE in water. To carry out the degradation process, a 100 mg of the nano-ZnO particles was used in a 500 ml solution of 100 ppm by weight of MTBE in deionized water. The photocatalytic degradation was conducted following the same procedure as described in example 1.

FIG. 3 results show that about 40% MTBE remains in the sample under investigation after 5 hours of UV light exposure.

Preparation of 0.5% Pd-nano ZnO and using the same as a photocatalyst to study degradation of MTBE in water: Pd-nano ZnO was prepared by doping 0.5 wt % of Pd on the synthesized nano-ZnO using wetness incipient impregnation method. A predetermined amount of palladium (II) nitrate dihydrate ($Pd(NO_3)_2.2H_2O$) was dissolved in deionized water to form enough solution to cover the required amount of nano-ZnO powder. The palladium nitrate impregnated nano-ZnO was dried at heating rate of 0.33° C./min from room temperature up to 85° C. and then exposed to ammonia vapors for 10 minutes. This step is performed to avoid melting of palladium nitrate before decomposition resulting high dispersion of nano Pd particles on ZnO. Palladium nitrate impregnated nano-ZnO was dried overnight in air at 100° C. The dried Pd/ZnO was calcined at 450° C. for 6 hours at a heating rate of 1° C./min to obtain 0.5%Pd-nano ZnO photocatalyst.

A 100 mg of the Pd-nano ZnO photocatalyst was used in a 500 ml solution of 100 ppm by weight of MTBE in deionized water in a photochemical reactor to investigate its catalytic properties. The catalytic experiment was conducted following the same procedure as described in the above example.

FIG. 3 results show 0.85 ppm of MTBE remains in the liquid sample after 5 hours of UV light exposure in the presence of 0.5%Pd-nano ZnO photocatalyst.

Example 4

Figure 4:
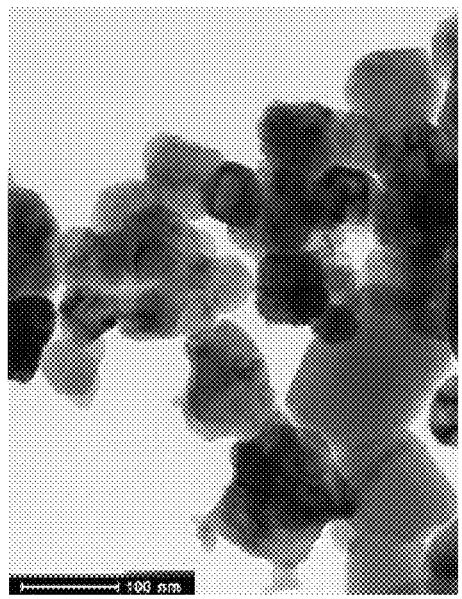
FIG. 4 shows the TEM image of nano 1.0% Pd/ZnO photocatalyst.
Figure 5:
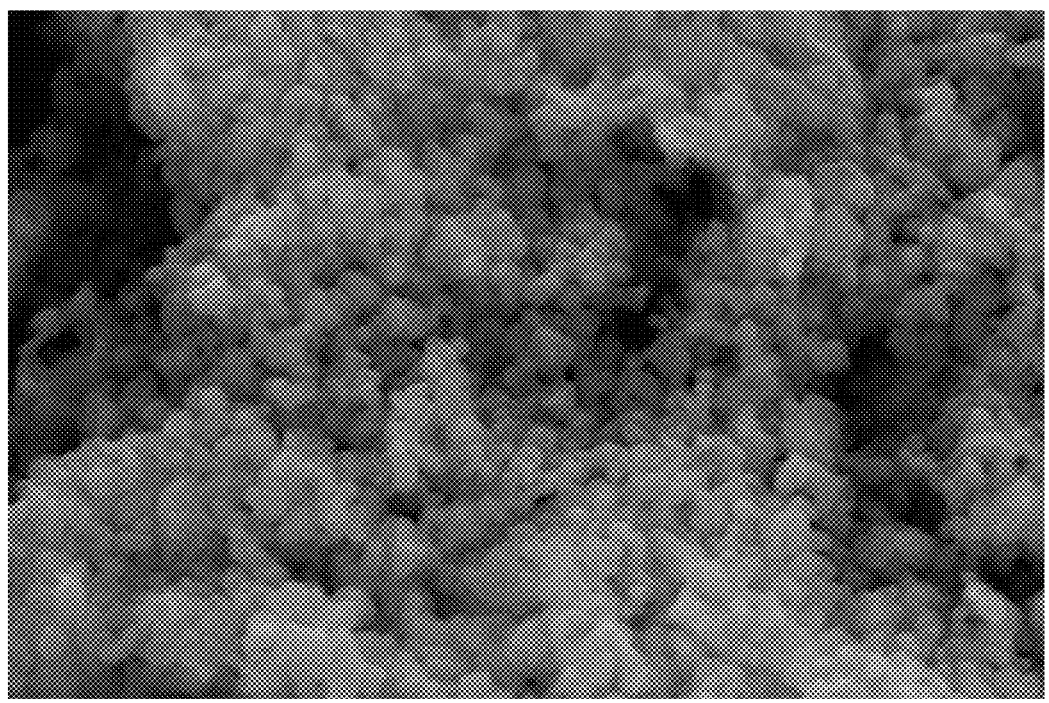
FIG. 5 shows the SEM image of nano 1.0% Pd/ZnO photocatalyst.

Preparation of 1.0% Pd-nano ZnO and using the same as a photocatalyst to study degradation of MTBE in water: 1.0% Pd-nano ZnO was prepared following the same procedure as adopted for making of 0.5% Pd-nano ZnO with 1.0%Pd doped on nano-ZnO. FIGS. 4 and 5 shows the TEM and SEM image of 1.0% Pd/ZnO respectively. Fine dispersion of Pd particles is clearly visible on nano scale ZnO particles in the range 40 to 100 nm.

A 100 mg of the 1.0% Pd-nano ZnO was used in a 500 ml solution of 100 ppm by weight of MTBE in deionized water in a photochemical reactor. The photocatalytic experiment was conducted following the same procedure as described in example 1.

FIG. 3 results show complete removal of MTBE from the sample under investigation after 4 hours of UV light exposure in the presence of 1.0Pd-nano ZnO photocatalyst. Thus the final result after 4 hours of UV exposure has 0.0 ppm MTBE on gas chromatograph that has minimum detection limit of less than 0.04 ppm.

Example 5

Preparation of 1.5% Pd-nano ZnO and using the same as a photocatalyst to study degradation of MTBE in water:1.5% Pd-nano ZnO was prepared following the same procedure as adopted for making 0.5% Pd-nano ZnO with 1.5% Pd doped onto nano-ZnO. A 100 mg of the 1.5% Pd-nano ZnO was then used in a 500 ml solution of 100 ppm by weight of MTBE in deionized water in a photochemical reactor. The photocatalytic experiment was conducted following the same procedure as described in above example 1.

FIG. 3 results show 3.9 ppm of MTBE remaining in the sample under investigation after 5 hours of UV light exposure in the presence of 1.5%Pd-nano ZnO photocatalyst.

Industrial Applicability

The presently disclosed invention provides a novel and useful photocatalyst composition and process for the removal of MTBE from ground water via photocatalytic degradation process. The photocatalyst and the process of using photocatalyst, as disclosed in the present application finds applicability in waste water treatment plants. The photocatalyst and the process of using photocatalyst, as disclosed in the present application finds applicability in degrading MTBE deposition resulting from oil spills or accidents involving fuel leakage. The photocatalyst and the process of using photocatalyst, as disclosed in the present application finds applicability in routine cleaning of fuel tanks both underground and above ground. The photocatalyst and the process of using photocatalyst, as disclosed in the present application finds applicability in marine spills cleaning which is huge problem for marine life. The photocatalyst and the process of using photocatalyst, as disclosed in the present application can also be implemented in nature using abundantly available solar light. In addition, it will be appreciated that the various compositions of making the photocatalyst and method of using the photocatalyst such as for photodegradation of toxic chemical such as MTBE in solution. Accordingly, the specification and drawings are to be regarded in an illustrative rather than a restrictive sense.

What is claimed is:

1. A method comprising;
   mixing a zinc nitrate hexahydrate and an ammonium carbonate to obtain nano zinc oxide particles;
   dissolving a pre-determined amount of a palladium (II) nitrate dehydrate $(Pd(NO_3)_2 \cdot 2H_2O)$ in deionized water comprising nano ZnO particles to form a palladium impregnated nano ZnO;
   drying the palladium impregnated nano ZnO overnight;
   exposing the palladium impregnated nano ZnO to ammonia vapors for a specific period of time;
   mixing and drying the palladium impregnated nano ZnO overnight; and
   calcining the dried palladium impregnated nano ZnO to obtain palladium doped nano zinc oxide photocatalyst.

2. The method of claim 1, wherein the pre-determined amount of Pd is in the range of 0.5% to 1.5%.

3. The method of claim 2, wherein the pre-determined amount of Pd is 0.5 wt % of Pd.

4. The method of claim 2, wherein the pre-determined amount of Pd is 1.0 wt % of Pd.

5. The method of claim 2, wherein the pre-determined amount of Pd is 1.5 wt % of Pd.

6. The method of claim 1, wherein calcination is carried at 500° C. for 3 hours at a heating rate of 1.5° C./min to obtain palladium doped nano zinc oxide photocatalyst.

7. The method of claim 1, wherein the photocatalyst is used for photocatalytic degradation of MTBE in water under UV light source.

8. The method of claim 1, wherein zinc nitrate hexahydrate and ammonium carbonate are mixed in the molar ratio of 1:1.

* * * * *